US012584877B2

(12) United States Patent

Haupt et al.

(10) Patent No.: US 12,584,877 B2

(45) Date of Patent: Mar. 24, 2026

(54) GAS MEASURING DEVICE AND METHOD FOR MEASURING CYANOGEN IN THE PRESENCE OF HYDROGEN CYANIDE

(71) Applicant: Dräger Safety AG & Co. KGaA, Lübeck (DE)

(72) Inventors: Stephan Haupt, Lübeck (DE); Andreas Nauber, Lübeck (DE); Michael Sick, Lübeck (DE); Tobias Reier, Lübeck (DE); Steffen Rittemann, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 462 days.

(21) Appl. No.: 17/928,968

(22) PCT Filed: May 27, 2021

(86) PCT No.: PCT/EP2021/064203

§ 371 (c)(1),
(2) Date: Dec. 1, 2022

(87) PCT Pub. No.: WO2021/244941

PCT Pub. Date: Dec. 9, 2021

(65) Prior Publication Data

US 2023/0221275 A1     Jul. 13, 2023

(30) Foreign Application Priority Data

Jun. 5, 2020     (DE) ..................... 10 2020 114 982.4

(51) Int. Cl.
G01N 27/27 (2006.01)
G01N 33/00 (2006.01)

(52) U.S. Cl.
CPC ......... G01N 27/27 (2013.01); G01N 33/0013 (2013.01); G01N 33/0037 (2013.01)

(58) Field of Classification Search
CPC .... G01N 27/27; G01N 27/16; G01N 33/0013; G01N 33/0037; Y02A 50/20
See application file for complete search history.

(56) References Cited

U.S. PATENT DOCUMENTS

| | | | |
|---|---|---|---|
| 4,703,646 A | 11/1987 | Muller et al. | |
| 6,001,383 A | 12/1999 | O'Brien et al. | |

(Continued)

FOREIGN PATENT DOCUMENTS

| | | | | |
|---|---|---|---|---|
| CN | 108490061 A | * | 9/2018 | ............... G01N 1/28 |
| DE | 2434930 A1 | | 2/1975 | |
| DE | 3729286 A1 | | 3/1989 | |
| DE | 3729286 C2 | | 8/1990 | |
| DE | 3923717 A1 | | 1/1991 | |
| DE | 10051106 A1 | | 5/2002 | |

(Continued)

OTHER PUBLICATIONS

Abe et al., The catalytic oxidation of cyanogen into nitric oxide and the intermediate product, the Journal of the Society of Chemical Industry, Japan, 1927, 30, 4B-5B (Year: 1927).*

(Continued)

*Primary Examiner* — Shizhi Qian

(74) *Attorney, Agent, or Firm* — McGlew and Tuttle, P.C.

(57) ABSTRACT

A gas measuring device (100) measures cyanogen in the presence of hydrogen cyanide. The gas measuring device (100) includes a measuring chamber (101), a heating element (103, 203) and an electrochemical sensor (105, 200). The measuring chamber (101) is configured to receive a sample. The heating element (103) is configured to thermally decompose cyanogen contained in the sample into decomposition products. The sensor (105, 200) is configured to detect the decomposition products of cyanogen, which are obtained by the thermal decomposition. A process measures cyanogen in the presence of hydrogen cyanide.

16 Claims, 3 Drawing Sheets

(56) References Cited

U.S. PATENT DOCUMENTS

| | | | | |
|---|---|---|---|---|
| 2001/0019844 A1* | 9/2001 | Kishkovich | .......... | G01N 33/007 |
| | | | | 436/106 |
| 2002/0043458 A1 | 4/2002 | Bernstein et al. | | |
| 2009/0114536 A1* | 5/2009 | Ishiguro | ............ | G01N 33/0016 |
| | | | | 204/406 |
| 2011/0308524 A1* | 12/2011 | Brey | ...................... | A62B 23/02 |
| | | | | 128/205.12 |
| 2012/0273846 A1* | 11/2012 | Neff | ................... | G01N 27/4141 |
| | | | | 257/253 |
| 2013/0046485 A1* | 2/2013 | Norman | ............. | G01N 33/0031 |
| | | | | 702/24 |
| 2018/0328873 A1* | 11/2018 | Maekawa | .......... | G01N 33/0037 |
| 2019/0317043 A1* | 10/2019 | Wei | ...................... | G01N 27/304 |

FOREIGN PATENT DOCUMENTS

| | | | | | |
|---|---|---|---|---|---|
| DE | 102010021975 A1 | 12/2011 | | | |
| EP | 2388580 A1 | 11/2011 | | | |
| JP | 2008076235 A | 4/2008 | | | |
| WO | WO-2009024774 A1 * | 2/2009 | ............. | G08B 17/00 |

OTHER PUBLICATIONS

Knowlton et al., Heat of combustion and formation of cyanogen, Journal of Research of the National Bureau of Standards, 1951, 46, 489-495 (Year: 1951).*

Campbell et al., Catalytic oxidation of cyanogen chloride over a monolithic oxidation catalyst, ERDEC-CR-219, 1997 (Year: 1997).*

Kröcher et al., Hydrolysis and oxidation of gaseous HCN over heterogeneous catalysts, Applied Catalysis B: Environmental, 2009, 92, 75-89 (Year: 2009).*

Zhao et al., Catalytic oxidation of HCN over 1 0.5% Pt/Al2O3 catalyst, Applied Catalysis B: Environmental, 2006, 65, 282-290 (Year: 2006).*

Lamoureux et al., Measurements and modelling of HCN and CN species profiles in laminar CH4/O2/N2 low pressure flames using LIF/CRDS techniques, Proceedings of the Combustion Institute, 2015, 35, 745-752 (Year: 2015).*

Bausone Bob: PureAire Air Check Advantage Methyl Bromide Monitor Instruction Manual, Dec. 18, 2019 URL: https://www.pureairemonitoring.com/wp-content/uploads/2020/01/Air-Check-Advantage-Methyl-Bromide-Manual-4.05.pdf [rech. Jan. 18, 2021].

PubChem. Bethesda (MD): National Library of Medicine (US), National Center for Biotechnology Information; 2004-. PubChem Annotation Record for Cyanogen, Source: Hazardous Substances Data Bank (HSDB); URL: https://pubchem.ncbi.nlm.nih.gov/source/hsdb/2130#section=Analytic-Laboratory-Methods-(Complete).

Glennon D., Caravello A., Ottmar S., Sweet C.: Web-Based Phosphine Fumigation Monitoring with Active Sensor Validation Confirms Lethality in Stored Grains, Julius-Kühn-Archiv, 2018, Nr. 463, S. 975-978. DOI 10.5073/jka.2018.463.213.

Dolman Chris: EDN(TM) Fumigas Introduction. Biosecurity Treatments 2014 Methyl Bromide and Alternatives Conference. URL http://www.fumigaciya.ru/sites/default/files/public/page/2011-09/15/ednfumigas.pdf [rech. Jan. 18, 2021].

* cited by examiner

1

GAS MEASURING DEVICE AND METHOD FOR MEASURING CYANOGEN IN THE PRESENCE OF HYDROGEN CYANIDE

CROSS REFERENCE TO RELATED APPLICATIONS

This application is a United States National Phase Application of International Application PCT/EP2021/064203, filed May 27, 2021, and claims the benefit of priority under 35 U.S.C. § 119 of German application 10 2020 114 982.4, filed Jun. 5, 2020, the entire contents of which are incorporated herein by reference.

TECHNICAL FIELD

The present invention pertains to a gas measuring device and to a process for measuring cyanogen (also known as dicyanogen and dicyan) in the presence of hydrogen cyanide (hydrocyanic acid).

TECHNICAL BACKGROUND

Fumigation, i.e., disinfection by fumigation, is a common method in agriculture for killing germs and bacteria on products that will later be used and sold in the food industry.

Fumigation was frequently carried out with methyl bromide in the past. Based on the highly carcinogenic effect, the use of methyl bromide for fumigation has already been banned in some countries. Cyanogen has proved to be effective as an alternative.

Since cyanogen frequently occurs during fumigation together with hydrogen cyanide (HCN), there is a need for measuring cyanogen in the presence of hydrogen cyanide.

Semiconductor sensors are used, as a rule, for measuring cyanogen, but they have a limited sensitivity and stability and they are not suitable as a result for the detection of an exceeding of a workplace limit value of 5 ppm or are suitable only conditionally.

Furthermore, cyanogen can be measured by a mass spectrometer. However, since mass spectrometers are unwieldy and complicated in use, these are likewise unsuitable for the detection of an exceeding of a workplace limit concentration of 5 ppm or are suitable for such use only conditionally.

JP 2008 076 235 A describes a process for measuring cyanogen, in which hydrogen sulfides are vaporized from a sample in order finally to measure the sample by means of a hydrogen cyanide gas sensor.

SUMMARY

Based on the above-described state of the art, a basic object of the present invention is to provide a possibility for measuring cyanogen, which is at least partially free from these drawbacks. One object of the present invention is therefore to provide a possibility for the reliable and simple detection of an exceeding of a permissible workplace limit value of cyanogen.

The above object is accomplished by features according to the invention. Features and details of the present invention appear from this disclosure, including the description and from the drawings. Features and details that are described in connection with the gas measuring device also apply, of course, in connection with the process according to the present invention and vice versa, so that reference is and can always mutually be made concerning the disclosure to the individual aspects of the present invention.

According to a first aspect, a gas measuring device is provided for measuring cyanogen in the presence of hydrogen cyanide for accomplishing the object. The gas measuring device comprises a measuring chamber, a heating element and an electrochemical sensor. The measuring chamber is configured to receive a sample. The heating element is configured to thermally decompose cyanogen contained in the sample. The sensor is configured to detect the decomposition products of the cyanogen, which are obtained by the thermal decomposition.

The gas measuring device according to the present invention is configured to determine a concentration of cyanogen in a sample even in the presence of hydrogen cyanide reliably and selectively as well as with a high sensitivity, especially with a sensitivity that makes it possible to detect cyanogen reliably beginning from a concentration of 1 ppm.

To measure a concentration of cyanogen in a sample, the gas measuring device being proposed comprises an electrochemical main sensor, which is used combined with a heating element, for example, with a heating wire or with a heating plate.

Since an electrochemical sensor cannot detect or measure cyanogen directly, provisions are made according to the present invention for the respective cyanogen molecules present in a sample to be decomposed thermally by means of the heating element. In particular, the heating element carries out a pyrolysis of the cyanogen molecules. Decomposition products, for example, nitrogen oxides or hydrogen cyanide, which can be detected by the electrochemical main sensor provided according to the present invention, are formed due to the thermal decomposition.

Provisions may be made for a temperature, which is set by means of the heating element for the thermal decomposition of respective cyanogen molecules, to be selected as a function of particular conditions present in the chamber of the gas measuring device proposed. As an alternative or in addition, it is conceivable that the temperature is set as a function of other reaction conditions, for example, a relative air humidity present in the chamber.

The heating element provided according to the present invention may be arranged freely in the chamber of the gas measuring device proposed. This means that the heating element and the sensor may be arranged separately from one another. As an alternative, a combined or integrated arrangement in a single or combined component is possible.

Furthermore, provisions may be made for the heating element to be configured to at least partially decompose cyanogen contained in the sample into nitrogen oxides and for the sensor to be configured to detect nitrogen oxides.

Since nitrogen oxides, for example, nitrogen monoxide and/or nitrogen dioxide, can be detected in a simple manner and accurately by means of an electrochemical sensor, a setting of the heating element to a temperature range for decomposing cyanogen into nitrogen oxides, i.e., into nitrogen monoxide and/or nitrogen dioxide, is especially advantageously suitable for operating the gas measuring device proposed.

Provisions may further be made for the gas measuring device to comprise a computing unit, which is configured to calculate a concentration of hydrogen cyanide contained in the sample on the basis of measured values determined by the sensor. Provisions may be made, as an alternative, for the gas measuring device to comprise a computing unit and for the sensor to be configured to detect hydrogen cyanide, wherein the computing unit is configured to calculate a concentration of hydrogen cyanide contained in the sample on the basis of measured values determined by means of the sensor during a first time period prior to a thermal decomposition by the heating element and to calculate a concentration of cyanogen contained in the sample on the basis of measured values determined by means of the sensor during a second time period after a thermal decomposition by the heating element.

A concentration of cyanogen in a particular sample can be inferred by means of a computing unit, for example, a computer or of any other form of programmable circuit with the use of, for example, a predefined coefficient of measured values determined by the sensor of the gas measuring device proposed. The sensor may be calibrated, for example, on the basis of a calibration sample in order to determine or to update the coefficient.

The sensor provided according to the present invention may be sensitive to hydrogen cyanide, and provisions are then made, in order to avoid an interaction of hydrogen cyanide already present in a particular sample with hydrogen cyanide generated by a thermal decomposition process, for the concentration of hydrogen cyanide that is already present in the sample to be determined prior to the thermal decomposition process. A concentration of cyanogen that was decomposed into hydrogen cyanide and a concentration of hydrogen cyanide that is originally present in the sample can correspondingly be inferred on the basis of a difference between measured values that were determined prior to the thermal decomposition process and after the thermal decomposition process.

Provisions may further be made for the gas measuring device to have a surface that acts as a catalyst during a thermal decomposition of cyanogen.

A temperature, which is to be provided by the heating element provided according to the present invention for a thermal decomposition process of cyanogen molecules, can be reduced by means of a catalyst or by a catalytic surface. Furthermore, respective decomposition products generated by the decomposition process can be influenced by a suitable selection of a material of a corresponding surface in combination with a suitable selection of a temperature set by the heating element, so that, for example, nitrogen oxides or hydrogen cyanide are formed by the decomposition process.

Further, provisions may be made for the surface to comprise at least one material from the following list of materials: Platinum, palladium, ruthenium, rhodium, iridium, and osmium.

Depending on the selection of the material or of the materials for the surface provided according to the present invention, more or less thermal energy is needed for the thermal decomposition. A correspondingly suitable heating element, which preferably has a minimal energy consumption, can be correspondingly selected depending on the selection of the material or of a combination of materials.

The material or the combination of materials of the surface provided according to the present invention may be provided directly or in a supported form on aluminum oxide, zirconium dioxide, silicon oxide, cerium oxide or ceramic.

Provisions may further be made for the sensor and for the heating element to be combined in an integrated component and for the heating element to be configured to heat a surface of the component.

A compact and energy-efficient measuring unit can be provided by means of an integrated component, which may be, for example, a pellistor with a pellistor bead. An outer surface of the pellistor bead may consist here of a catalytic material, which reduces the quantity of energy needed for a thermal decomposition process.

Provisions may further be made for the heating element or a combination of a heating element and a surface to be configured to decompose cyanogen contained in the sample into nitrogen oxide or into hydrogen cyanide.

A decomposition product generated during a thermal decomposition process can be precisely predefined by a joint effect of heating element and catalytic surface. In particular, the catalytic surface or an introduction of energy provided by the heating element may be selected to be such that nitrogen oxides or hydrogen cyanide will be formed.

Provisions may further be made for the measuring chamber to comprise a filter unit permeable to cyanogen and impermeable to hydrogen cyanide.

In order to minimize the influence of hydrogen cyanide on the detection of cyanogen, the gas measuring device being proposed may comprise a filter, which prevents hydrogen cyanide from entering into the chamber of the gas measuring device. As an alternative, the filter unit may be a membrane, for example, a PTFE membrane, which is permeable to hydrogen cyanide and cyanogen and is configured to minimize flow effects on a detection by means of the sensor provided according to the present invention.

Provisions may further be made for the gas measuring device to comprise a pump for introducing a sample into the measuring chamber.

The gas measuring device being proposed may be based as a passive gas measuring device on the principle of diffusion or comprise a pump by means of which a sample can be taken actively from an environment and introduced into the chamber of the gas measuring device.

Provisions may further be made for the gas measuring device to comprise an auxiliary sensor, wherein the sensor is configured to detect nitrogen oxides and the auxiliary sensor is configured to detect hydrogen cyanide.

Concentrations of both gases, i.e., of cyanogen and of hydrogen cyanide, can be determined by means of two sensors, i.e., a sensor for detecting nitrogen oxides and an auxiliary sensor for detecting hydrogen cyanide.

In a second aspect, the invention being proposed pertains to a process for measuring cyanogen in the presence of hydrogen cyanide, wherein the process comprises a provision step for providing a possible embodiment of the gas measuring device being proposed, a feed step for feeding a sample into the measuring chamber of the gas measuring device, a decomposition step for the thermal decomposition of cyanogen present in the sample by means of the heating element of the gas measuring device and a detection step for detecting decomposition products of the cyanogen, which was generated by the decomposition step, by means of the sensor of the gas measuring device.

The process being proposed is used especially to operate the gas measuring device proposed.

Provisions may be made for the process to comprise, furthermore, a detection step for the detection of hydrogen cyanide. The detection of hydrogen cyanide may be used additionally for the detection of decomposition products in order to determine information on a concentration of hydrogen cyanide in a sample in addition to information on a concentration of cyanogen. As an alternative, the detection of hydrogen cyanide may be carried out in order to detect decomposition products per se.

Provisions may further be made for the detection of hydrogen cyanide by means of the sensor to be carried out in a first detection step chronologically before the thermal decomposition and in a second detection step chronologically after the thermal decomposition.

Further actions improving the present invention appear from the following description of some exemplary embodiments of the present invention, which are shown in the figures. All the features and/or advantages appearing from the claims, from the description or from the drawings, including design details and arrangements in space, may be essential for the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
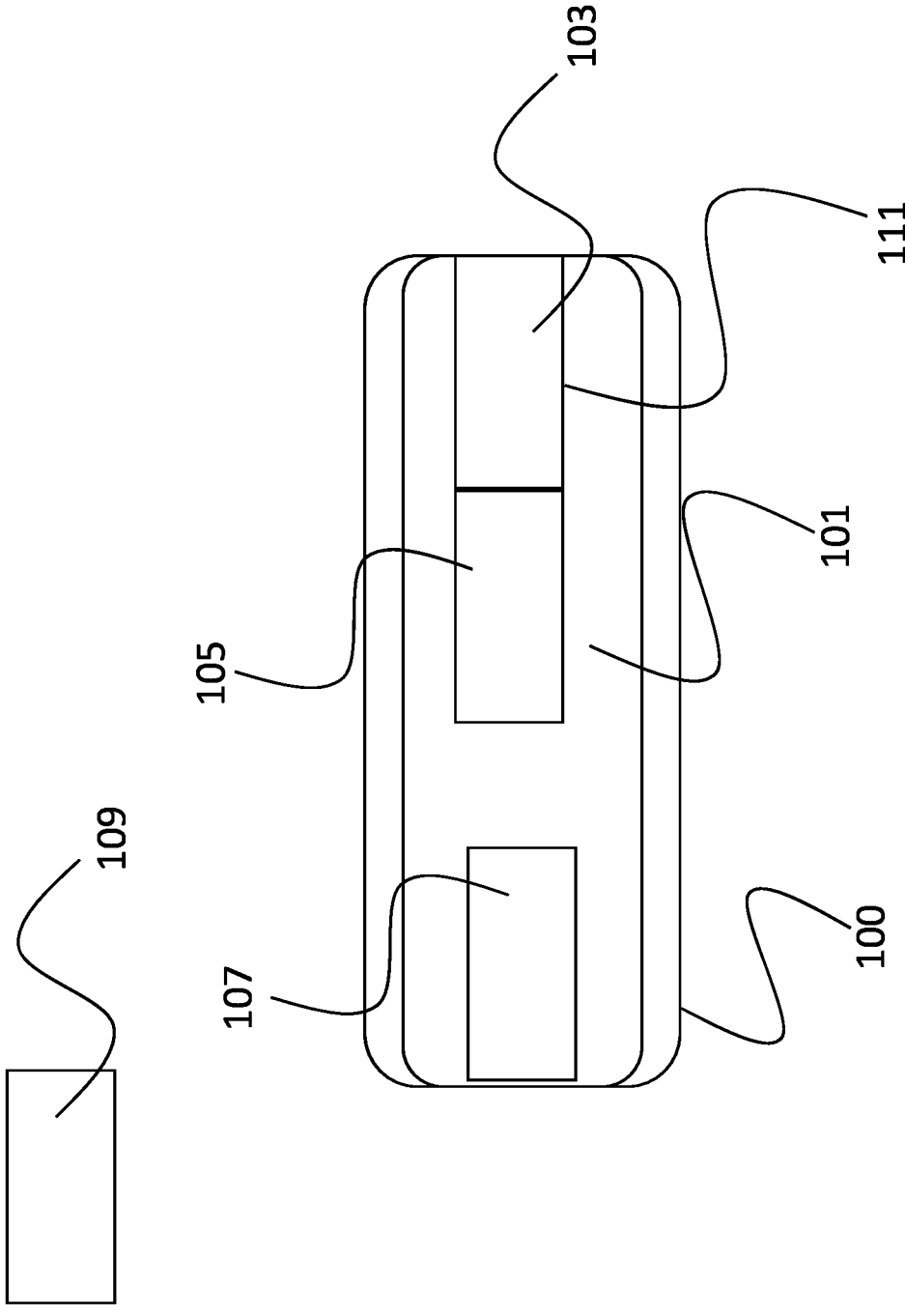
FIG. 1 is a schematic view of an embodiment of the gas measuring device according to the present invention.

Referring to the drawings, FIG. 1 shows a gas measuring device 100. The gas measuring device 100 comprises a measuring chamber 101, a heating element 103 and an electrochemical sensor 105.

To measure a concentration of cyanogen in the presence of hydrogen cyanide, a sample present in the measuring chamber 101 is heated by means of the heating element 103 and is, as a result, thermally decomposed. The decomposition products formed by the thermal decomposition are detected by means of the sensor 105. A concentration of cyanogen in the sample can be inferred, for example, with the use of an optional computing unit 107 on the basis of measured values determined by the sensor 105.

As an alternative, measured values determined by the sensor 105 can be used directly to display a concentration of cyanogen in the sample. The sensor 105 may be connected to this end, for example, to an output unit 109, for example, to a display and/or to a speaker.

Provisions may be made for the computing unit 107 to be configured to output a warning by means of the output unit 109 when a concentration of cyanogen or hydrogen cyanide present in a particular sample is above a predefined threshold value.

The gas measuring device 100 is a mobile or portable gas measuring device with a power source in this case, so that the gas measuring device can be used "in the field."

In order to minimize the energy demand for a thermal decomposition of cyanogen molecules in the sample and to control a decomposition process into selected decomposition products, for example, nitrogen oxides or hydrogen cyanide, a catalytic surface 111 may be arranged in the chamber 101, especially at the heating element 103.

Figure 2:
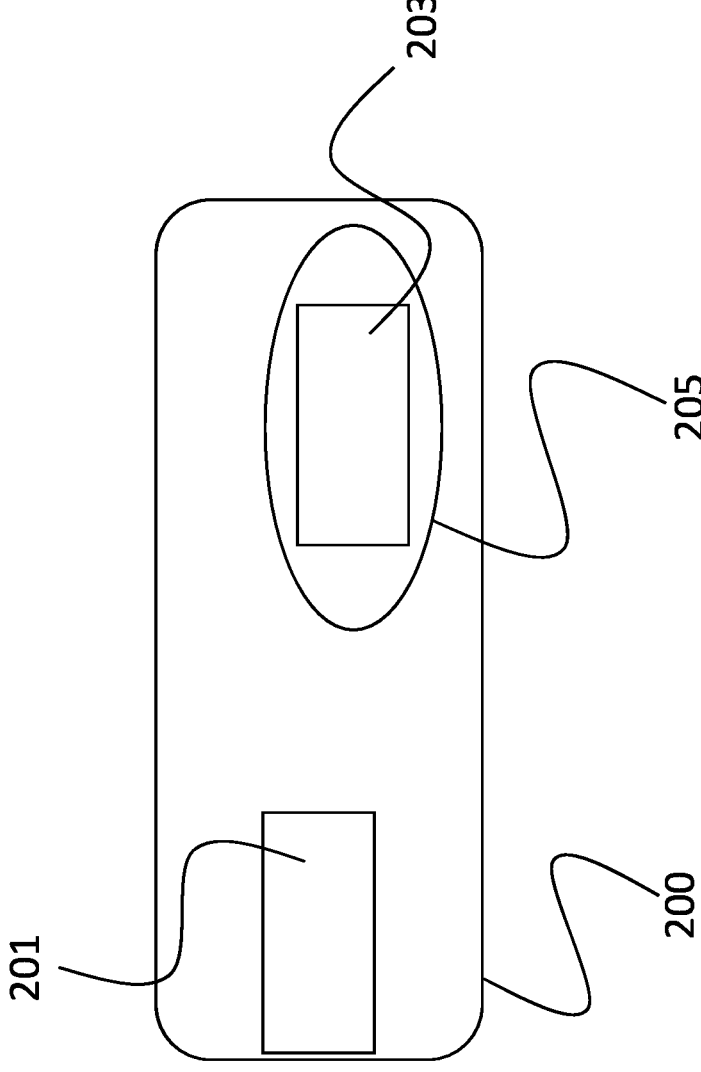
FIG. 2 is a schematic view of another embodiment of the sensor provided according to the present invention.

FIG. 2 shows a sensor 200. The sensor 200 is an integrated component and comprises a measuring electrode 201, a heating element 203 and a catalytic surface 205 in the form of a pellistor bead, which encloses the heating element 203 and is configured as an integral component of the heating element 203. Thermal energy generated by the heating element 203 is correspondingly transferred to the catalytic surface 205.

As soon as a cyanogen molecule comes into contact with the catalytic surface 205, the cyanogen molecule is decomposed thermally into, for example, nitrogen dioxide and carbon dioxide based on the thermal energy introduced into the catalytic surface 205 and based on the catalytic properties of the catalytic surface 205.

The sensor 200 is configured specifically for the detection of nitrogen dioxide and it correspondingly determines a measured value as a function of a measured concentration of nitrogen dioxide. The determined measured value is correspondingly proportional to a concentration of cyanogen and makes it possible to assess whether a cyanogen concentration in an environment is above or below a predefined threshold value.

Figure 3:
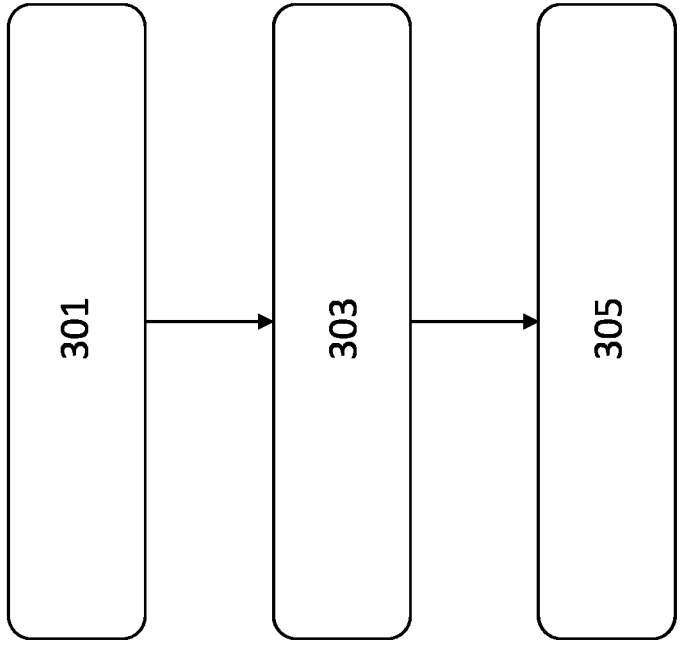
FIG. 3 is a flow diagram showing a course of a process according to the present invention.
Figure 3:
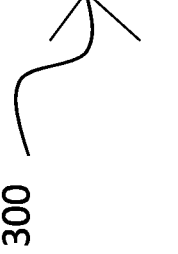

FIG. 3 shows a process 300. The process 300 comprises a provision step 301 for the provision of a possible embodiment of the gas measuring device being proposed, a feed step 303 for feeding a sample into the measuring chamber of the gas measuring device, a decomposition step for the thermal decomposition of cyanogen present in the sample by means of the heating element of the gas measuring device, and a detection step 305 for the detection of decomposition products of the cyanogen, which are generated by the decomposition step, by means of the sensor of the gas measuring device.

While specific embodiments of the invention have been shown and described in detail to illustrate the application of the principles of the invention, it will be understood that the invention may be embodied otherwise without departing from such principles.

LIST OF REFERENCE NUMBERS

100 Gas measuring device
101 Measuring chamber
103 Heating element
105 Sensor
107 Computing unit
109 Output unit
111 Catalytic surface
200 Sensor
201 Measuring electrode
203 Heating element
205 Catalytic surface
300 Process
301 Provision step
303 Feed step
305 Detection step

The invention claimed is:

1. A gas measuring device for measuring cyanogen in the presence of hydrogen cyanide, the gas measuring device comprising:

a measuring chamber;

a heating element;

an electrochemical sensor, wherein the measuring chamber is configured to receive a sample, wherein the heating element is configured to thermally decompose the cyanogen contained in the sample into decomposition products, wherein the electrochemical sensor is configured to detect the decomposition products of the cyanogen, which are obtained by the thermal decomposition; and a surface, which acts as a catalyst during the thermal decomposition of the cyanogen, wherein the surface comprises at least one material from the following list of materials: platinum, palladium, ruthenium, rhodium, iridium, and osmium, wherein the measuring chamber comprises a filter unit that is permeable to the cyanogen and is impermeable to the hydrogen cyanide.

2. The gas measuring device in accordance with claim 1, wherein the heating element is configured to decompose the cyanogen contained in the sample at least partially into nitrogen oxides, and the electrochemical sensor is configured to detect the nitrogen oxides.

3. The gas measuring device in accordance with claim 1, further comprising: a computing unit configured to calculate a concentration of the cyanogen contained in the sample based on measured values determined by the electrochemical sensor during a time period after the thermal decomposition of the sample by the heating element.

4. The gas measuring device in accordance with claim 1, wherein the electrochemical sensor and the heating element are combined into an integrated component and the heating element is configured to heat a surface of the integrated component.

5. The gas measuring device in accordance with claim 1, wherein the heating element or a combination of the heating element and the surface is configured to decompose the cyanogen contained in the sample into nitrogen oxide or to hydrogen cyanide.

6. The gas measuring device in accordance with claim 1, further comprising a pump for introducing the sample into the measuring chamber.

7. The gas measuring device in accordance with claim 1, wherein the electrochemical sensor or the heating element or the electrochemical sensor and the heating element comprises a pellistor bead.

8. The gas measuring device in accordance with claim 1, wherein the electrochemical sensor is configured to detect nitrogen oxides.

9. A process for measuring cyanogen in the presence of hydrogen cyanide, wherein the process comprises:

providing a gas measuring device comprising a measuring chamber configured to receive a sample, a heating element configured to thermally decompose the cyanogen contained in the sample into decomposition products, an electrochemical sensor configured to detect the decomposition products of the cyanogen, which are obtained by the thermal decomposition, and a surface configured to act as a catalyst during the thermal decomposition of the cyanogen, wherein the surface comprises at least one material selected from the group consisting of platinum, palladium, ruthenium, rhodium, iridium, and osmium, wherein the measuring chamber comprises a filter unit that is permeable to the cyanogen and is impermeable to the hydrogen cyanide;

feeding the sample into the measuring chamber of the gas measuring device;

thermally decomposing the cyanogen present in the sample by means of the heating element of the gas measuring device; and detecting the decomposition products of the cyanogen, which are generated by the thermal decomposition, by means of the electrochemical sensor of the gas measuring device.

10. A gas measuring device for measuring an indication of cyanogen in a sample, the gas measuring device comprising:

a measuring chamber configured to receive the sample;

a heating element operatively disposed relative to the measuring chamber and configured to thermally decompose the cyanogen contained in the sample into decomposition products;

a catalytic surface operatively disposed relative to the measuring chamber and configured to act as a catalyst during the thermal decomposition of the cyanogen, the catalytic surface comprising a material selected from the group consisting of platinum, palladium, ruthenium, rhodium, iridium, and osmium; and an electrochemical sensor operatively disposed relative to the measuring chamber and configured to detect one or more of the decomposition products of the cyanogen, which are obtained by the thermal decomposition.

11. The gas measuring device in accordance with claim 10, further comprising a computing unit configured to determine the indication of a concentration of the cyanogen based on measured values of the one or more of the decomposition products determined by the electrochemical sensor.

12. The gas measuring device in accordance with claim 11, wherein:

the heating element or a combination of the heating element and the catalytic surface is configured to decompose the cyanogen contained in the sample into nitrogen oxide or at least partially into nitrogen oxides or into hydrogen cyanide; and the electrochemical sensor is configured to detect the nitrogen oxide, or the nitrogen oxides, or the hydrogen cyanide.

13. The gas measuring device in accordance with claim 12, wherein the computing unit is configured to calculate a concentration of the cyanogen contained in the sample based on measured values determined by the electrochemical sensor during a time period subsequent to the thermal decomposition of the sample by the heating element.

14. The gas measuring device in accordance with claim 11, wherein:

the electrochemical sensor and the heating element are comprised by an integrated component;

the catalytic surface is comprised by a surface of the integrated component; and the heating element is configured to heat the surface of the integrated component.

15. The gas measuring device in accordance with claim 11, further comprising an auxiliary sensor, wherein the electrochemical sensor is configured to detect nitrogen oxides and the auxiliary sensor is configured to detect hydrogen cyanide.

16. The gas measuring device in accordance with claim 11, wherein the measuring chamber comprises a filter unit that is permeable to the cyanogen and is impermeable to hydrogen cyanide.

\*   \*   \*   \*   \*